(12) United States Patent
Wiberg et al.

(10) Patent No.: US 8,272,384 B2
(45) Date of Patent: Sep. 25, 2012

(54) FIXATION DEVICE

(75) Inventors: Kristian Wiberg, Alvsjö (SE); Thomas Arn, Lindingö (SE); Anders Fischer, Nyköping (SE)

(73) Assignee: Elekta AB (Publ), Stockholm (SE)

( * ) Notice: Subject to any disclaimer, the term of this patent is extended or adjusted under 35 U.S.C. 154(b) by 211 days.

(21) Appl. No.: 12/766,639

(22) Filed: Apr. 23, 2010

(65) Prior Publication Data
US 2010/0275926 A1    Nov. 4, 2010

(30) Foreign Application Priority Data
Apr. 30, 2009  (EP) ..................... 09159184

(51) Int. Cl.
*A61G 15/00*  (2006.01)
(52) U.S. Cl. ......... 128/845; 128/859; 378/208; 606/130
(58) Field of Classification Search .............. 606/130; 128/846, 859, 861–862; 378/208
See application file for complete search history.

(56) References Cited

U.S. PATENT DOCUMENTS

| | | | |
|---|---|---|---|
| 4,979,519 A * | 12/1990 | Chavarria et al. ............ | 128/857 |
| 5,219,288 A | 6/1993 | Kawamura et al. | |
| 5,464,411 A * | 11/1995 | Schulte et al. ............... | 606/130 |
| 5,730,745 A | 3/1998 | Schulte et al. | |
| 6,424,694 B1 | 7/2002 | Molteni et al. | |
| 6,459,927 B1 | 10/2002 | Franklin et al. | |

FOREIGN PATENT DOCUMENTS

| | | |
|---|---|---|
| DE | 196 19 761 A1 | 11/1996 |
| EP | 0 365 840 A1 | 5/1990 |
| GB | 2 213 066 A | 8/1989 |

* cited by examiner

*Primary Examiner* — Patricia Bianco
*Assistant Examiner* — Camtu Nguyen
(74) *Attorney, Agent, or Firm* — Birch, Stewart, Kolasch & Birch, LLP

(57) ABSTRACT

The present invention relates to the field of radiation therapy and radiation surgery. In particular, the invention relates to devices and methods for stereotactic medical procedures and it provides for repeated accurate positioning (fixation) of a patient, or a part of a patient, for carrying out medical procedures which are done at different times such as fractionated radiation therapy. Specifically, a patient fixation device for fixating a head of a patient relatively a treatment unit as a preparation for treatment or during treatment of the head is provided. The patient fixation device being is adapted to be attached to a stereotactic frame structure connected to the treatment unit. The attachment means is adapted to be releasably attached to corresponding attachment plates attached to teeth of the upper jaw or maxilla of the patient, each attachment plate being fixated to at least one tooth by means of an adhesive, wherein the attachment means allows removal from the attachment plates of the patient and re-attachment to the corresponding attachment plates of the patient with an identical orientation relatively the frame structure and the teeth of the patient.

20 Claims, 9 Drawing Sheets

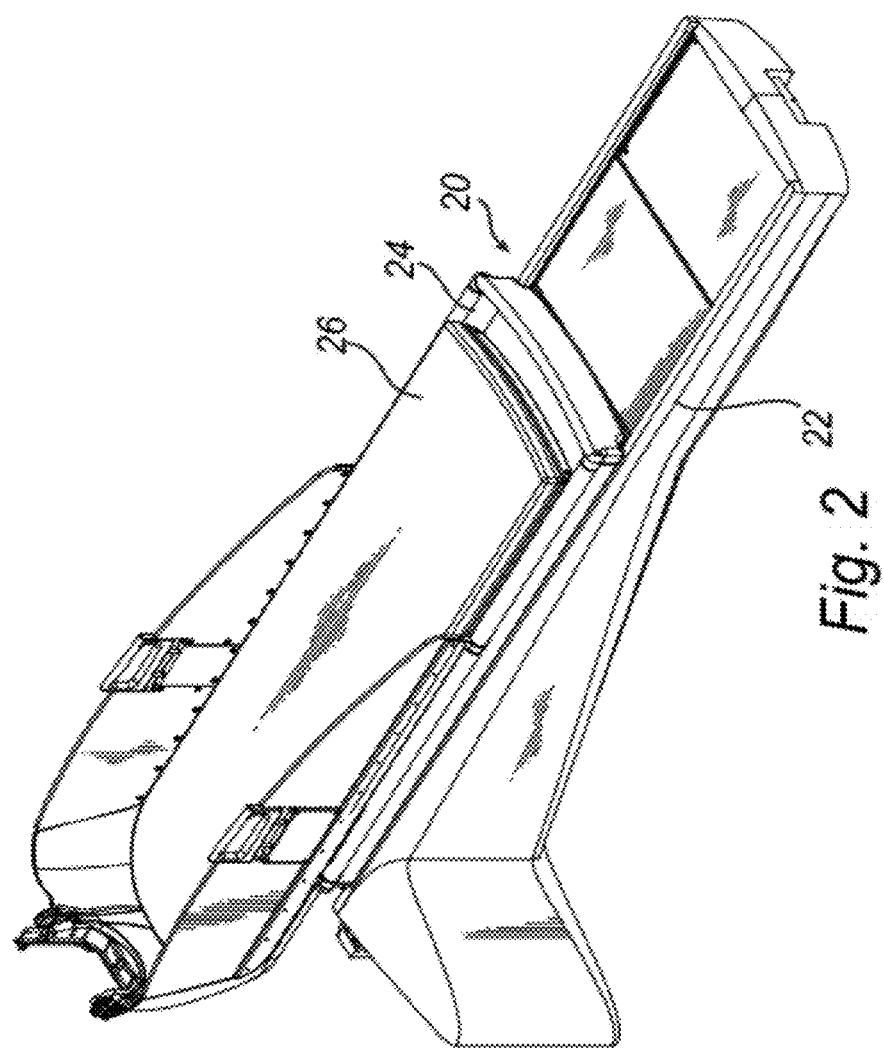
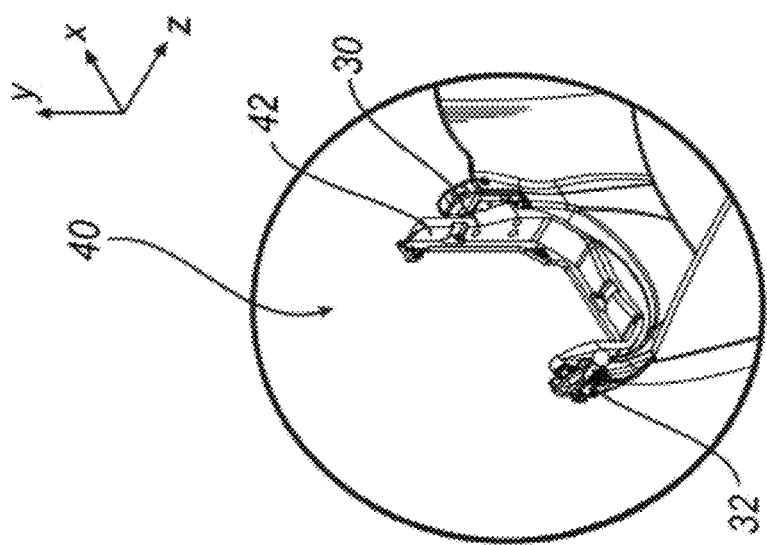
Fig. 2
Fig. 3

FIXATION DEVICE

FIELD OF THE INVENTION

The present invention relates to the field of radiation therapy and radiation surgery. In particular, the invention relates to devices and methods for stereotactic medical procedures and it provides for repeated accurate positioning (fixation) of a patient, or a part of a patient, for carrying out medical procedures which are done at different times such as fractionated radiation therapy. Further, the present invention may also be used in other medical procedures or medical therapies outside radiotherapy where a need for repeat fixation of a patient or a portion of a patient exists such as where a first medical procedure is performed requiring a precise location of the patient or portions of the patient and, at some later point in time, a second medical procedure is performed on the patient where a precise location of the patient or portions of the patient is required.

BACKGROUND OF THE INVENTION

The development of surgical techniques has made great progress over the years. For instance, for patients requiring brain surgery, non-invasive surgery is now available which is afflicted with very little trauma to the patient.

Stereotactic radiation surgery is such a minimally invasive treatment modality that allows delivery of a large single dose of radiation to a specific intracranial target while sparing surrounding tissue. Unlike conventional fractionated radiation therapy, stereotactic radiation surgery does not rely on, or exploit, the higher radiation sensitivity of neoplastic lesions relative to normal brain (therapeutic ratio). Its selective destruction depends primarily on sharply focused high-dose radiation and a steep dose gradient away from the defined target. The biological effect is irreparable cellular damage and delayed vascular occlusion within the high-dose target volume. Because a therapeutic ratio is not required, traditionally radiation resistant lesions can be treated. Because destructive doses are used, however, any normal structure included in the target volume is subject to damage.

One such non-invasive radiation therapy technique is so called LINAC (Linear Accelerator) radio therapy or radiation therapy. In a LINAC radiation therapy system, a collimated x-ray beam of a very high energy level is focused on a stereotactically identified intracranial target. In such an accelerator, electrons are accelerated to near light speed and are collided with a heavy metal, e.g. tungsten. The collision mainly produces heat but a small percentage of the energy is converted into highly energetic photons, which, because they are electrically produced, are called "x-rays". The gantry of the LINAC rotates around the patient, producing an arc of radiation focused on the target. The couch in which the patient rests is then rotated in the horizontal plane, and another arc is performed. In this manner, multiple non-coplanar arcs of radiation intersect at the target volume and produce a high target dose, resulting in a minimal radiation affecting the surrounding brain.

Another system for non-invasive surgery is sold under the name of Leksell Gamma Knife®, which provides such surgery by means of gamma radiation. The radiation is emitted from a large number of fixed radioactive sources and is focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all radiation sources intersect or converge, causing the radiation to reach tissue-destructive levels. The point of convergence is hereinafter referred to as the "focus point". Such a gamma radiation device is, for example, referred to and described in U.S. Pat. No. 4,780,898.

In the system, the head of a patient is immobilized in a stereotactic instrument which defines the location of the treatment volume in the head. Further, the patient is secured in a patient positioning unit which moves the entire patient so as to position the treatment volume in coincidence with the focus point of the radiation unit of the radiation therapy system.

Consequently, in radiation therapy systems, such as a LINAC system or a Leksell Gamma Knife® system, it is of a high importance that the positioning unit which moves the patient so as to position the treatment volume in coincidence with the focus point of the radiation unit of the system is accurate and reliable. That is, the positioning unit must be capable of position the treatment volume in coincidence with the focus point at a very high precision. This high precision must also be maintained over time. In order to further reduce potential damage of healthy tissue, medical procedures performed by means of a LINAC system or a Leksell Gamma Knife® system often involve repeated treatment at different times so called fractionated therapy. A routine course of radiation therapy may span anywhere from 10 to 64 fractions over a period of two to six weeks. The number of treatments depends on the specifics of the particular disease. For each fraction the patient must be repositioned at the radiation therapy unit and aligned relative to the radiation beam or beams at a highly precise degree of accuracy.

Hence, in order to obtain as favourable clinical effect as possible during the therapy is it of an utmost importance that the radiation reaches and hits the target, i.e. the treatment volume, with a high precision and thereby spares the healthy tissue being adjacent to and/or surrounding the treatment volume. To achieve this, the patient must be immobilized during each therapy session and, moreover, the position of the head of the patient must be exactly the same in each therapy session as in the reference position, i.e. the position during the session when the pictures to create the therapy plan were captured by means of, for example, Computerized Tomography Imaging (CT-imaging).

Consequently, in fractionated radiation therapy where the patient is docked in and out of the radiation therapy system at each therapy session, it must be secured that the patient is positioned in exactly the same position and orientation relative the radiation beam or beams as in the session when the pictures were captured to create the therapy plan and in exactly same position as in the preceding therapy sessions.

One prior art method for enabling measurements of the head of a patient and for immobilizing or fixating the head of the patient during neurological diagnosis, therapy or surgery, in particular during radiation therapy relatively an interface unit, frame or adaptor adapted to be fixated to a radiation therapy unit is a stereotactic frame provided with pin support members in form of posts having fixation pins for invasive fixation to the skull of a patient. In use during therapy or diagnostics, the stereotactic frame is arranged around the head of a patient, and the fixation pins of the posts connected to the frame are screwed into or to abutment against the bone of the skull, thus ensuring a rigid fixation of the reference system. The frame is then rigidly held in position in relation to a patient table. This kind of frame is obviously not suitable for fractionated therapy.

Other prior art methods more suitable for fractionated therapy involves mouth pieces or bite-block shaped after upper palate of the patient and is thus adapted to be received in the mouth of the patient, i.e. containing an impression of the teeth of the patient, and support structure and the stereotactic frame for connecting the mouth-piece or bite block with the therapy unit. During a therapy session, the patient bites the mouth-piece or bite-block and the mouth-piece or bite-block is fixated to the upper palate of the patient by means of a low pressure or vacuum pump device connected to the mouth-piece via tubings. Further, the mouth-piece or bite-block is adapted to be fixated relatively the support structure and stereotactic frame and, thus, relatively the therapy unit.

However, there is still a need within the art for improved means for repeat fixation of a patient in radiotherapy and, more generally, there is a need for improved means for repeat fixation of a patient also in therapies outside radiotherapy such as stereotactic radio surgery.

SUMMARY OF THE INVENTION

Thus, an object of the present invention is to provide an improved device, system and method for repeated fixation of a patient in performing medical procedures such as stereotactic radiosurgery or radiation therapy.

A further object of the present invention is to provide an improved device, system, and method for accurate and highly precise non-invasive repeat fixation of a patient in performing medical procedures such as stereotactic radiosurgery or radiation therapy.

Yet another object of the present invention is to provide an improved device, system, and method for stereotactic radiotherapy.

Still another object of the present invention is to provide an improved device, system, and method for relatively fast repositioning of a patient after an initial positioning of the patient.

These and other objects are achieved by providing a fixation device having the features defined in the independent claim. Example embodiments are defined in the dependent claims.

It should be noted that the term "treatment" as used herein, e.g. "treatment unit", "treatment system" or "treatment of the head", is intended to refer to any kind of diagnosis, therapy or surgery inside the head of the patient, e.g. MRI, Biopsy, neurological diagnosis, therapy or surgery, or various radiation therapy treatment or the like. Thus, a treatment unit may for example be a radiation therapy unit, proton therapy unit, ultrasound therapy or the like. The embodiments of the invention are especially suitable for a fractionated treatment, e.g. a fractionated radiation therapy.

The term "medical device" as used herein is intended to refer to any kind of devices used for diagnosis, therapy or surgery inside the head of the patient, e.g. a biopsy needle or the like.

It should also be noted that the term "frame" as used herein is intended to refer to an element for supporting another element, e.g. for supporting a medical device. In such a case, the frame, for instance a stereotactic frame, provides a support for the medical device that is used for performing the treatment.

In the present application reference is being made to a coordinate system coordinate system, the system being a Cartesian coordinate system defined by three orthogonal axis having an x-axis extending in the medial-lateral direction of the patient, an y-axis extending in the anterior-posterior direction, and a z-axis extending in the cranial-caudal direction.

According to a first aspect of the present invention, there is provided a patient fixation device for fixating a head of a patient relatively a treatment unit as a preparation for treatment or during treatment of the head. The patient fixation device being is adapted to be attached to a stereotactic frame structure connected to the treatment unit. The attachment means is adapted to be releasably attached to corresponding attachment plates attached to teeth of the upper jaw or maxilla of the patient, each attachment plate being fixated to at least one tooth by means of an adhesive, wherein the attachment means allows removal from the attachment plates of the patient and re-attachment to the corresponding attachment plates of the patient with an identical orientation relatively the frame structure and the teeth of the patient.

According to a second aspect of the present invention, there is provided a patient fixation system for fixating a head of a patient relatively a treatment unit as a preparation for treatment or during treatment of the head. The patient fixation system is adapted to be attached to a stereotactic frame structure connected to the treatment unit and comprises attachment plates adapted to be attached on teeth of the upper jaw or maxilla of the patient, each attachment plate being fixated to at least one tooth by means of a dental adhesive; and attachment means adapted to be releasably attached to corresponding attachment plates wherein the attachment means allows removal from the attachment plates of the patient and re-attachment to the corresponding attachment plates of the patient with an identical orientation relatively the frame structure and the teeth of the patient.

According to a third aspect of the present invention, there is provided a method for fixating a head of a patient relatively a treatment unit as a preparation for treatment or during treatment of the head using a fixation system according to the second aspect of the present invention. The method comprises the steps, not necessarily in order, of: fixating the attachment plates on teeth of the maxilla of the patient, each attachment plate being fixated to at least one tooth by means of a dental adhesive; positioning a patient for a first medical procedure; attaching the interface means to the stereotactic frame structure; attaching the attachment means to corresponding attachment plates provided on teeth of the upper jaw or maxilla of the patient; performing the first medical procedure on the patient; removing the attachment means after completion of the first medical procedure; and re-attaching the attachment means to corresponding attachment plates provided on teeth of the maxilla of the patient a later time, wherein the attachment means is re-attached to the corresponding attachment plates of the patient with an identical orientation relatively the frame structure and the teeth of the patient as when the attachment means was previously attached.

Thus, the present invention is based on the idea of gluing fixation plates or attachment plates to teeth of the maxilla (upper jaw) using a dental adhesive, which provides a firm fixation of the individual plates to the teeth. Each plate can be applied on one tooth or several teeth. Further, attachment means is adapted to be releasably attached to the attachment plates hence allowing removal from the attachment plates of the patient and re-attachment to the corresponding attachment plates of the patient with an identical orientation relatively the frame structure and the teeth of the patient. The attachment plates are glued in place at a setup session and the attachment means for connecting to the plates is adjusted to the tooth configuration and the location of the attachment plates on teeth of the patient and is then attached. If used in fractionated therapy, the attachment plates are left on the teeth between successive therapy sessions. After a medical procedure (e.g. a radiation therapy session) has been performed on the patient, the attachment means can be removed by disconnecting it from the attachment plates. At a later time, when a next medical procedure (e.g. a subsequent radiation therapy session in a fractionated treatment of the patient) is to be performed, the attachment means can be docked to the patient, i.e. the attachment means can be re-attached to the attachment plates, at the identical orientation relatively the patient (or portion of the patient) and relatively the radiation therapy system or the therapy unit.

In one embodiment of the present invention, the patient fixation device being is adapted to be releasable attached to a stereotactic frame structure connected to the treatment unit.

According to an embodiment of the present invention, an interface unit connected to the attachment means is adapted to be releasably mounted in the frame structure.

According to an embodiment of the present invention, the attachment means further comprises: a first attachment member including an attachment element adapted to be releasably attached to a corresponding at least one first attachment plate, a second attachment member including an attachment element adapted to be releasably attached to a corresponding at least one second attachment plate, and a third attachment member including an attachment element adapted to be releasably attached to a corresponding at least one third attachment plate. This construction provides a high degree of flexibility and adjustability both during the set-up session, when the fixation device or fixation system is adapted to a specific patient, and during treatment such as fractionated radiation therapy when the patient is docked into and out of the treatment unit.

In accordance with an embodiment of the present invention, the first attachment member includes an arm being pivotally connected to the interface unit to allow the arm to be adjusted relatively the interface unit in two dimensions, the arm including the attachment element arranged at a distal part of the arm and being adapted for releasable connection to a corresponding attachment plate; and wherein the second attachment member includes an arm being pivotally connected to the interface unit to allow the arm to be adjusted relatively the interface unit in two dimensions, the arm including the attachment element arranged at a distal part of the arm and being adapted for releasable connection to a corresponding attachment plate.

In an embodiment of the present invention, the first and second arm is connected to each other by means of a locking element and wherein respective arm is connected to the interface unit via pivot means, wherein respective arm can be turned relatively the interface means and relatively each other in two dimension in an un-locked state and respective arm can be fixated relatively the interface means and relatively each other in a locked state.

According to an embodiment of the present invention, the third attachment member includes an arm and the attachment element arranged at a distal end of the arm and being adapted for releasable connection to a corresponding attachment plate, wherein the arm is pivotally connected to the interface unit.

In one embodiment of the present invention, the arm of the third attachment member is connected to the interface unit by means of a ball and socket joint, wherein the arm can be adjusted in three dimensions relatively the interface unit in an un-locked state.

According to an embodiment of the present invention, the attachment means comprises fiducials, the fiducials being radio-opaque markers for computer tomography (CT) scanning or magnetic resonance markers for magnetic resonance (MR) scanning.

In one embodiment of the present invention, the first and second arm, respectively, is adapted to have an adjustable length and include a respective locking means, wherein a length of a respective arm can be adjusted in an un-locked state and can be locked at a desired length.

According to an embodiment of the present invention, the attachment means adapted to be releasably attached to corresponding attachment plates attached to teeth of the maxilla of said patient is a bite-block shaped as a cast of the teeth of the maxilla of the patient. Thus, the attachment means is casted after the teeth of the upper jaw of the patient and can be fixated to the plates, in turn, attached to the teeth. The bite-block can be connected to the frame directly or via the interface unit by means of support arms. The bite-block can be made, for example, by introducing the bite-block filled with a material that can be shaped in a non-solidified form. The patient then clenches his or her teeth about the bite-block and thereby the bite-block is shaped after the teeth and when the material of the bite-block has solidified, a cast of the teeth has been created. The bite-block can be attached to the plates attached to the teeth by means of attachment elements, which for example, may be holes adapted to received corresponding balls of the attachment plates, or vice versa. Other embodiment may include, for example, means for attaching the bite-block by means of screws, snap connections, or stretched elastic bands.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

BRIEF DESCRIPTION OF THE DRAWINGS

Preferred embodiments of the invention will now be described in greater detail with reference to the accompanying drawings, in which

FIG. 2 illustrates the positioning unit used in the system of FIG. 1;

FIG. 3 illustrates a part of the positioning unit including the engagement points for holding a fixation frame in more detail;

DETAILED DESCRIPTION

Figure 1:
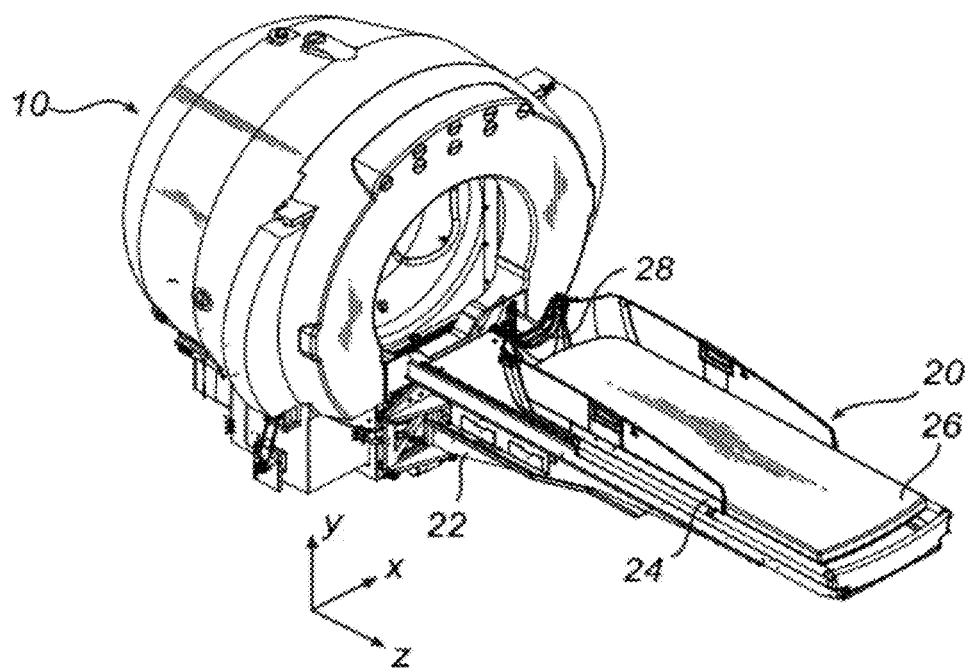
FIG. 1 illustrates the general principle of a radiation therapy system in which the present invention may be used.

First, with reference to FIGS. 1-3, a radiation therapy system, e.g. a Leksell Gamma Knife® system, in which the present invention may be used, will be described. However, as will be appreciated from the following detailed description, the present invention may also be used in other radiation therapy systems such as the LINAC system where fractionated therapy is common. Furthermore, the present invention may be used in other medical procedures or medical therapies outside radiotherapy where a need for repeat fixation of a patient or a portion of a patient exists such as where a first medical procedure is performed requiring a precise location of the patient or portions of the patient and, at some later point in time, a second medical procedure is performed on the patient where a precise location of the patient or portions of the patient is required. It might be possible to repeat laborious and time-consuming localizations steps for the second medical procedure at the expense of increased medical costs and complexity. As used herein, the term "medical procedure" is a procedure for diagnostic and/or remedial purposes.

The radiation therapy system comprises a radiation therapy unit or radiation unit 10 and a patient positioning unit 20 will be described. In the radiation unit 10, there are provided radioactive sources, radioactive source holders, a collimator body, and external shielding elements. The collimator body comprises a large number of collimator channels directed towards a common focus point, in a manner as is commonly known in the art.

The collimator body also acts as a radiation shield preventing radiation from reaching the patient other than through the collimator channels. Examples of collimator arrangements in radiation therapy systems applicable to the present invention can be found in U.S. Pat. No. 6,931,096, which is hereby incorporated herein by reference in its entirety. However, the present invention is also applicable to radiation therapy systems using other arrangements for collimating radiation into a fixed focus point, such as is disclosed in U.S. Pat. No. 4,780,898. Furthermore, the fixation device according to the present invention is also applicable to LINAC radiosurgical systems, in which a collimated x-ray beam is focused on a stereotactically identified intracranial target and the gantry of the LINAC rotates around the patient, producing an arc of radiation focused on the target.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and firmly hold a patient fixation device or system according to the present invention, either directly or via an adaptor unit 42, see FIG. 3.

The fixation arrangement 28 comprises two engagement points 30, 32, which are arranged for preventing the patient fixation system from translational and/or rotational movement in relation to the movable carriage 24.

Accordingly, in FIGS. 1-3 a radiation therapy system for providing gamma radiation therapy to a target volume in the head of human patient is illustrated. Such radiation therapy is often referred to as stereotactic radiation surgery. During a therapy session, the patient head is fixed relative the therapy system via a fixation unit and a stereotactic head frame, which comprises engagement points adapted for engagement with the engagement points 30, 32 of the radiation therapy system. Conventionally, a bite-block shaped after upper palate of the patient, i.e. containing an impression of the teeth of the patient, and thus adapted to be received in the mouth of the patient is connected to the support structure or the stereotactic frame. During a therapy session, the patient bites the bite-block and the bite-block is fixated to the upper palate of the patient by means of a low pressure or vacuum pump device connected to the mouth-piece via tubings. Further, the mouth-piece or bite-block is adapted to be fixated relatively the support structure and stereotactic frame and, thus, relatively the therapy unit. During movement of the treatment volume in the head of the patient in relation to the radiation focus point, along the three orthogonal axes x, y, and z shown in FIG. 1, the entire patient is moved along the axes. Thus, there is no relative movement between the head frame and the carriage 24 of the patient positioning unit 20. The present invention is instead based on the idea of attaching or fixating the frame directly to the teeth of the patient. As will be described in detail hereinafter, attachment plates are fixated to the teeth of the patient by means of a dental adhesive. A fixation device including attachment means can then be fixated or attached to the attachment plates, which fixation device can be releasably and firmly docked to the stereotactic frame. Thereby, the patient can be immobilized relative the treatment unit in accurate and non-invasive manner since the fixation device can be removed and reconnected to the plates in exactly the same orientation and position as many times as needed.

Figure 4:
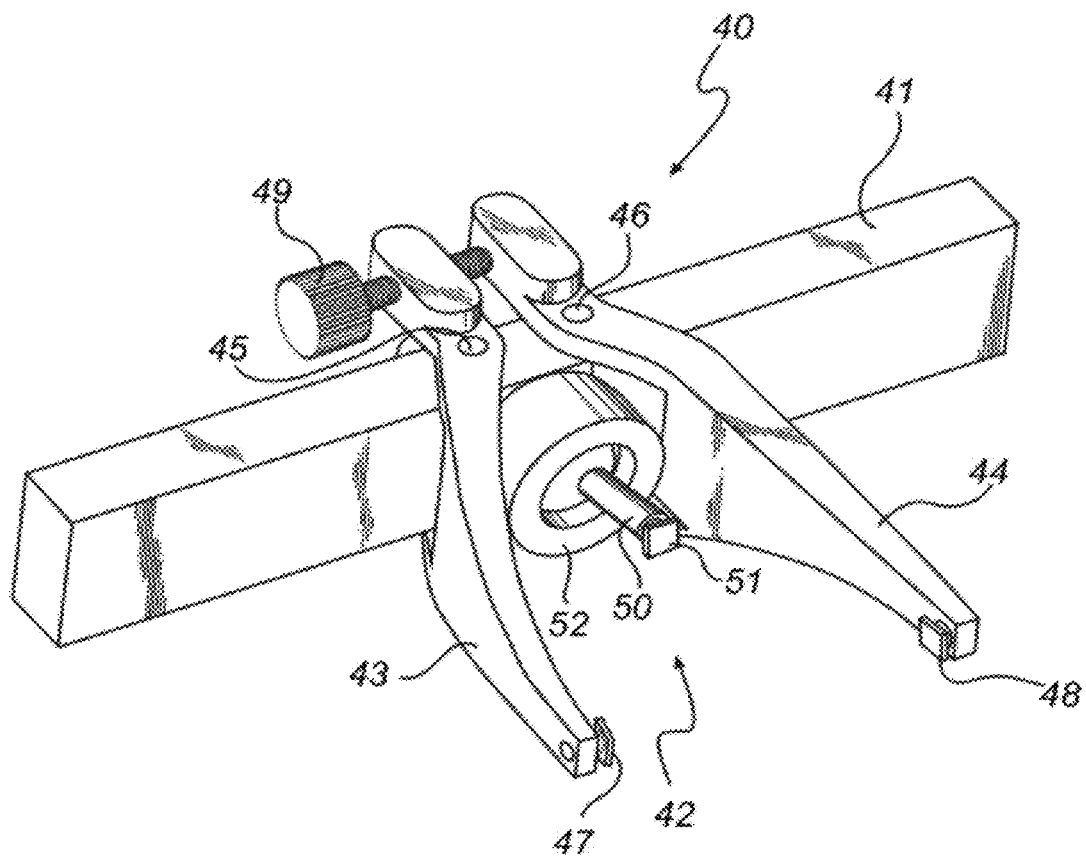
FIG. 4 schematically illustrates an embodiment of the fixation device according to the present invention.
Figure 5:
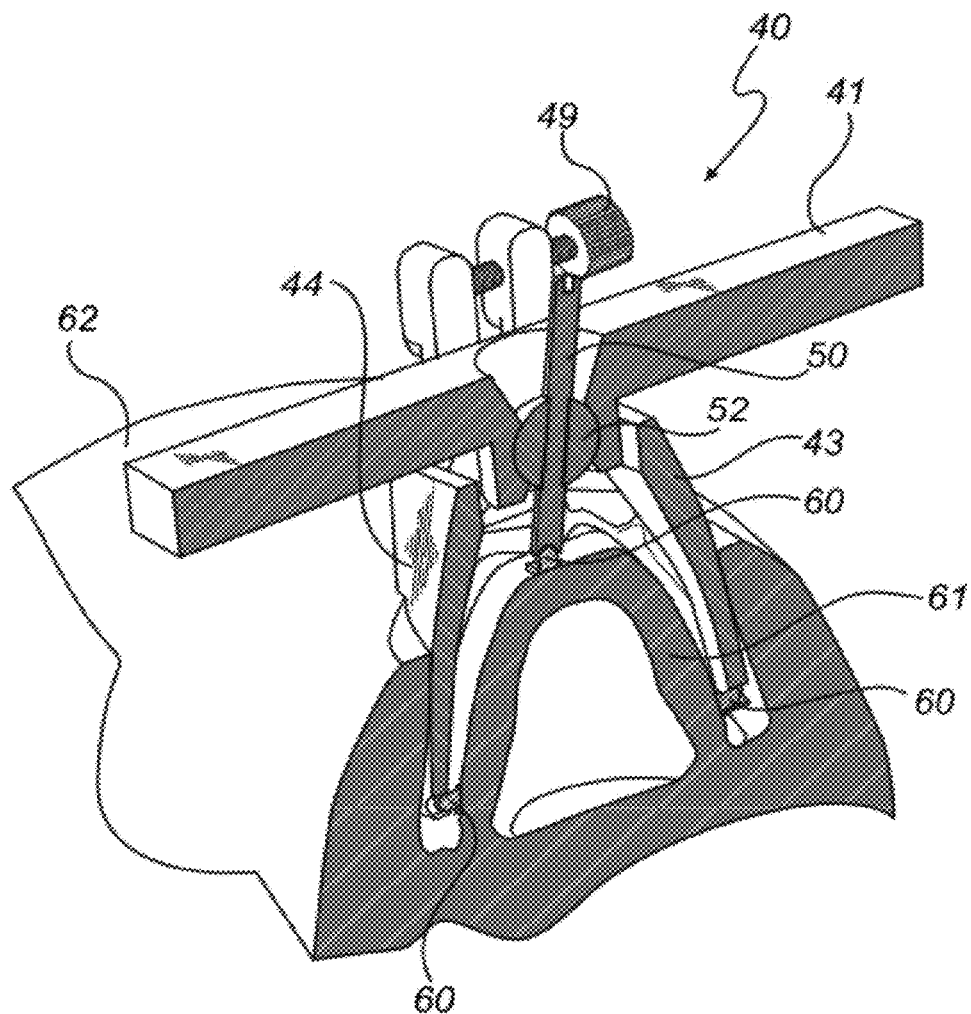
FIG. 5 schematically illustrates an embodiment of a fixation system including the fixation device shown in FIG. 4 in a cross-sectional view attached to a patient.
Figure 6:
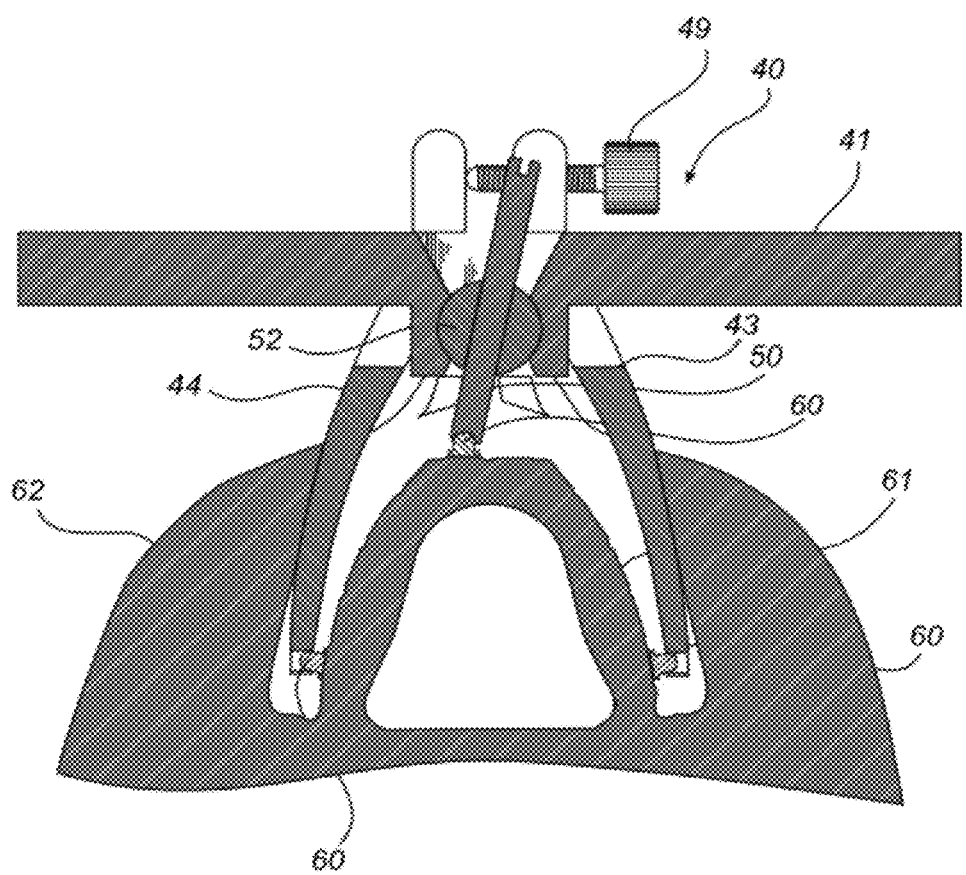
FIG. 6 schematically illustrates the embodiment of the fixation system shown in FIG. 5 in a cross-sectional view attached to a patient.
Figure 7:
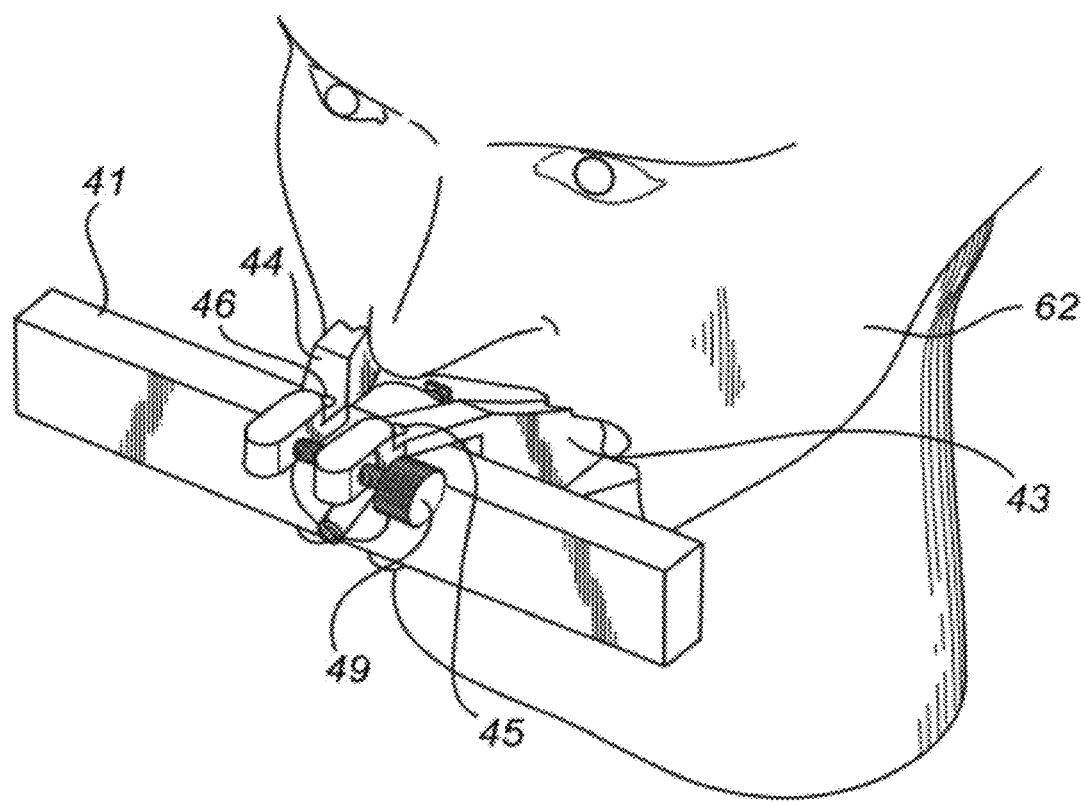
FIG. 7 schematically illustrates a front view of the embodiment of the fixation system shown in FIG. 5.

Turning now to FIG. 4-7, an embodiment of the present invention will be discussed in detail. In FIG. 4, a perspective view of a fixation device according an embodiment of the present invention is schematically illustrated. The fixation device 40 comprises an interface unit 41 adapted to be mounted at or connected to a stereotactic frame and attachment means 42 adapted to be releasably attached to corresponding attachment plates 60 provided on teeth 61 of the maxilla or upper jaw of a patient 62 (see FIGS. 5 and 6). Each attachment plate 60 is fixated to at least one tooth 61 by means of a dental adhesive providing a firm fixation being impervious over time. The attachment plates 60 can be based on a similar technology used for braces, which is a known and proven technology, and a dental adhesive used in such applications can also be used for attaching the attachment plates 60.

The attachment plate 60 may include a ball for engagement with a corresponding joint of the attachment means 42, or, a joint for engagement with a corresponding ball of the attachment means 42. Accordingly, the attachment means 42 allows removal from the attachment plates 60 and re-attachment to the corresponding attachment plates 60 with an identical orientation relatively the stereotactic frame and the teeth 61 of the patient 62. The attachment means 42 comprises a first arm 43 and a second arm 44 pivotally connected to the interface unit 41 at a first pivot point 45 and at a second pivot point 46, respectively. Thereby, the first arm 43 and the second arm 44 can be turned relatively the interface unit 42 and relatively the teeth 61 of the patient 62 in an un-locked state in a yx-plane, i.e. a plane extending in the medial-lateral direction and in the anterior-posterior direction of the patient. The first arm 43 comprises an attachment element 47, which, in this embodiment, is a socket, for connection to a corresponding attachment plate 60, which, in this embodiment, includes a ball. Further, the second arm 44 comprises an attachment element 48, which, in this embodiment, is a socket, for connection to a corresponding attachment plate 60, which, in this embodiment, includes a ball. As mentioned above, the first and second arm 43 and 44, respectively, is pivotally connected to the interface unit 41. In an un-locked state, the arms 43 and 44 can be turned relatively the teeth to facilitate detachment from and reconnection to the attachment plates 60. When attached to the attachment plates 60, the arms can be locked at a desired mutual relationship and relatively the interface means 41 by means of a looking screw 49. Respective attachment element 47 and 48 is arranged at a distal part of the first and second arm 43 and 44, respectively, and can be adjusted relatively the corresponding attachment plate 60. For example, the respective attachment element 47 and 48 can be connected to respective arm 43 and 44 by means of a ball and socket joint.

Furthermore, the attachment device 42 also includes a third central arm 50 including at least one attachment element 51 arranged at a distal end of the arm 50. The attachment element 51 is adapted for releasable connection to a corresponding attachment plate 60. In this embodiment, the attachment element 51 is a socket, for connection to a corresponding attachment plate 60, which, in this embodiment, includes a ball. The third arm 50 is pivotally connected to the interface unit 41 via a ball and socket joint 52. Thereby, the third arm can be adjusted in three dimensions relatively the interface unit 41 and the corresponding attachment plate 60. That is, in all three orthogonal axis in a coordinate system having an x-axis extending in the medial-lateral direction of the patient, an y-axis extending in the anterior-posterior direction, and a z-axis extending in the cranial-caudal direction. Further, the attachment element 51 can be adjusted relatively the arm by means of a ball and socket joint 52. Preferably, the third arm 50 is adjusted to a desired orientation relatively the interface unit 41 and the corresponding attachment plate 60 at a set-up session and is the locked in this position and orientation such that the desired position and orientation can be maintained during the complete therapy, i.e. in a fractionated therapy during all therapy sessions.

Figure 8:
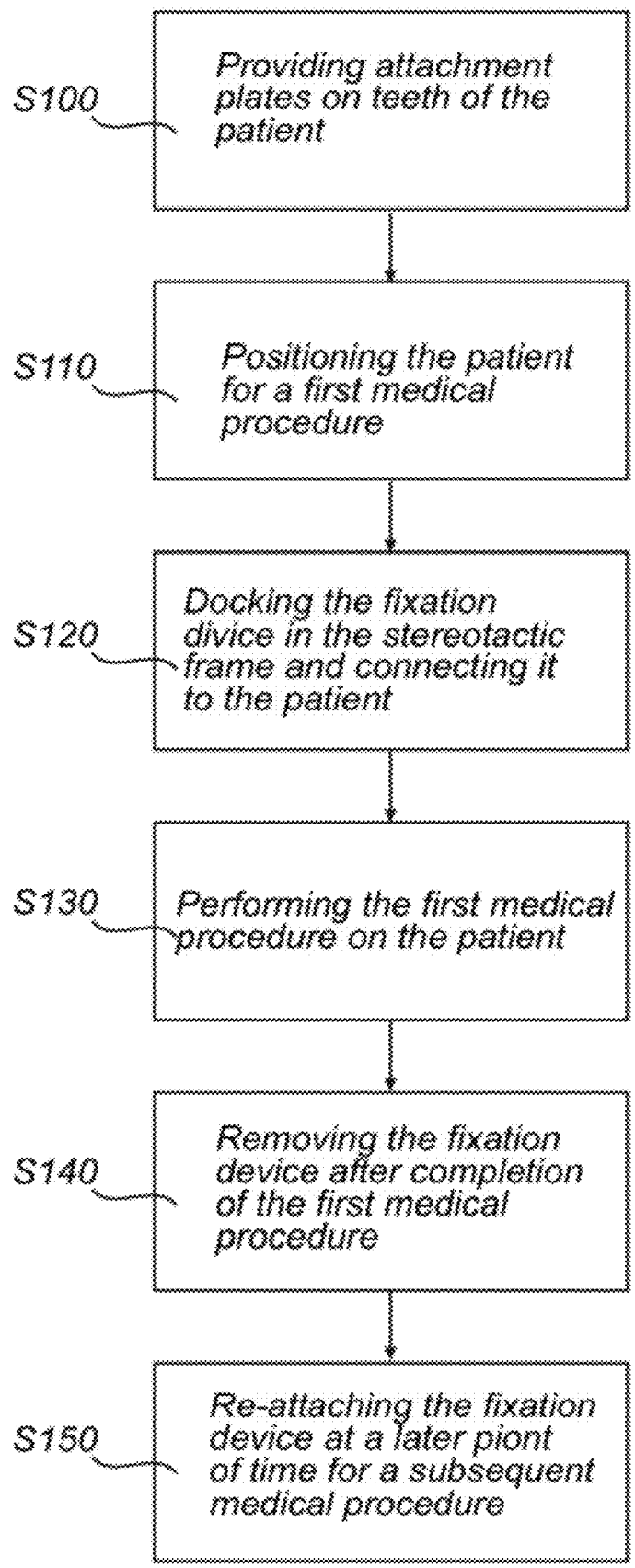
FIG. 8 shows a flow chart of a method according to the present invention.

With reference now to FIG. 8, a method for fixating a head of a patient relatively a treatment unit as a preparation for or during treatment of the head using a fixation system according to the present invention will be briefly described. However, it should be noted that the steps described hereinafter are not necessarily conducted in the order given below and as illustrated in FIG. 8. As have been discussed above, the present invention may be used in a Leksell Gamma Knife® system, but, also in other radiation therapy systems such as the LINAC system where fractionated therapy is common.

The treatment of a radiation therapy patient can be broken down into four stages. These are (a) diagnostic evaluation, (b) treatment planning, (c) simulation, and (d) treatment. The present invention mainly relates to step (d) but may be applicable in step (a), (b) or (c). In step (a), the physician decides which tissues are at risk of disease and should be targeted. The patient may undergo diagnostic tests including angiography, computerized tomography (CT) and magnetic resonance (MR) imaging. To this end, the attachment device 42 may include fiducial markers being radio-opaque markers for computer tomography (CT) scanning or magnetic resonance markers for magnetic resonance (MR) scanning. After the tissues at risk have been identified, treatment planning and simulation steps are performed, which involves obtaining a set of images such as plane films, digital images, CT, MRI, and ultrasound images.

First, at step 100, the attachment plates are attached to the teeth of the maxilla of the patient and each attachment plate being fixated to at least one tooth by means of a dental adhesive. In one preferable embodiment of the present invention, three attachment plates are fixated to the teeth of the patient, see for example, FIGS. 5 and 6. The use of three connection points will give a stable and reliable fixation of the fixation device to the patient. More than three connection points is also conceivable. For example, one further embodiment may include five connection points. That is, two attachment plates are placed on the teeth such that a first arm (corresponding to the first arm 43 but provided with two attachment elements) can be connected and firmly attached, two attachment plates are placed on the teeth such that a second arm (corresponding to the second arm 44 but provided with two attachment elements) can be connected and firmly attached, and one attachment plate is placed on the front teeth such that the third arm 50 can be connected and firmly attached. Then, at step 110, a patient can be positioned for a first medical procedure. At step 120, the interface means 41 can be attached to the stereotactic frame structure and the attachment means 42 is attached to the corresponding attachment plates 60 provided on teeth of the maxilla of the patient. Subsequently, at step 130, a first medical procedure can be performed on the patient. As discussed above, the present invention is suitable for use in fractionated radiation therapy and preparation steps for such a therapy such as treatment planning and simulation steps are performed, which involving obtaining a set of images such as plane films, digital images, CT, MRI, and ultrasound images. Further, the present invention may also be used in other medical procedures or medical therapies outside radiotherapy where a need for repeat fixation of a patient or a portion of a patient exists such as where a first medical procedure is performed requiring a precise location of the patient or portions of the patient and, at some later point in time, a second medical procedure is performed on the patient where a precise location of the patient or portions of the patient is required. Thus, as used herein, the term "medical procedure" is a procedure for diagnostic and/or remedial purposes.

Subsequently, at step 140, after completion of the first medical procedure, the attachment means 42 or the fixation device 40 can be removed and then, at step 150, at a later point of time when a second medical procedure is to be conducted, the attachment means 42 can be re-attached to corresponding attachment plates 60 or the fixation device 40 can be re-attached to the attachment plates 60 and docked into the stereotactic frame, wherein the attachment means 42 can be re-attached to the corresponding attachment plates 60 with an identical orientation relatively the frame structure and the teeth of the patient as when the attachment means was previously attached. It should be noted that the steps described above not necessarily have to be conducted in the order as illustrated in FIG. 8. For example, in one embodiment, step S120 may be conducted before step S110 instead for subsequently.

Figure 9:
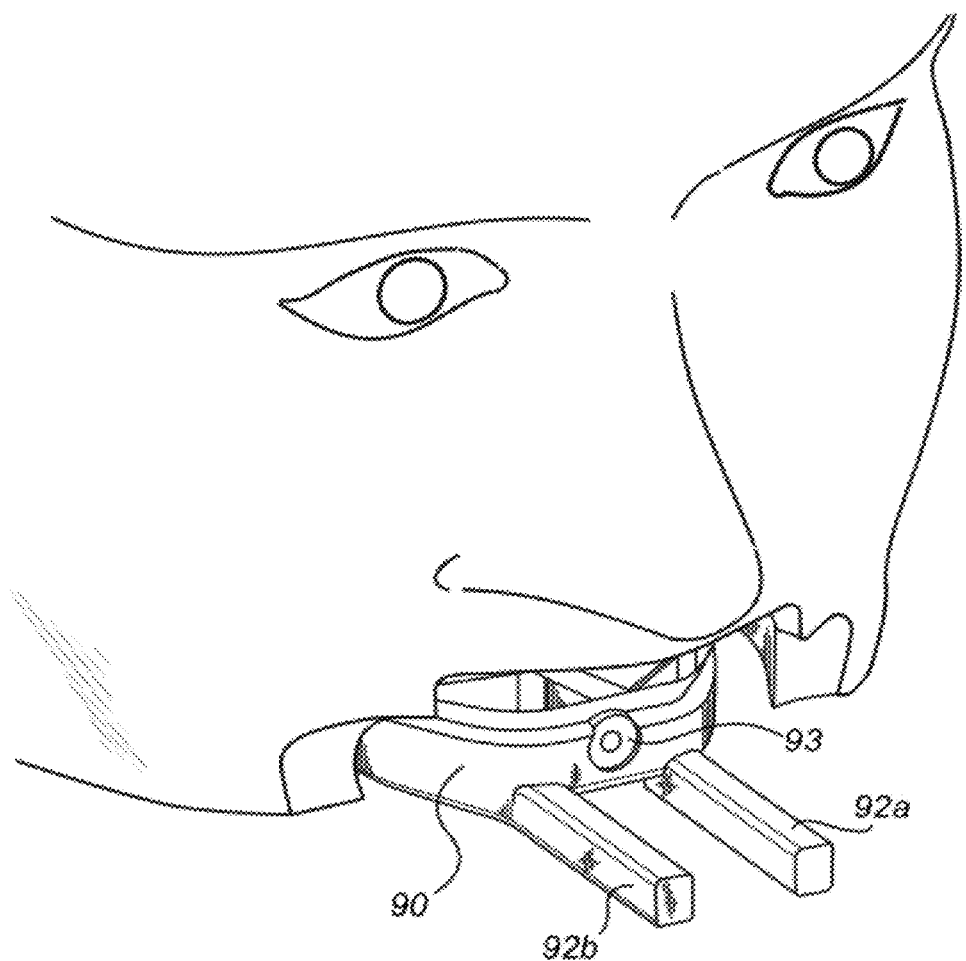
FIG. 9 schematically illustrates a further embodiment of the fixation device according to the present invention.
Figure 10:
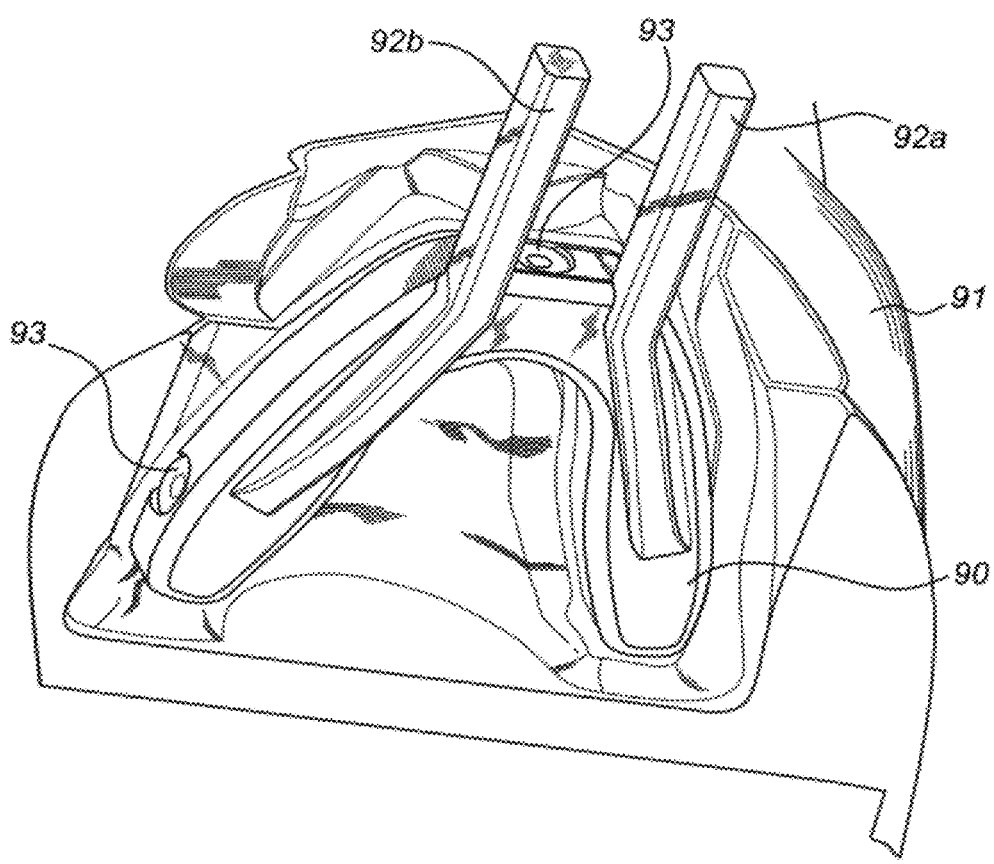
FIG. 10 schematically illustrates an embodiment of a fixation system including the fixation device shown in FIG. 9 in a cross-sectional view attached to a patient.

With reference now to FIGS. 9 and 10, an embodiment of the present invention will be discussed. In this embodiment, the attachment means 90 is adapted to be releasably attached to corresponding attachment plates (not shown) attached to teeth of the maxilla of the patient 91 is a bite-block shaped as a cast of the teeth of the maxilla of the patient 91. The bite-block 90 is connected to the frame directly or via the interface unit by means of support arms 92a and 92b. The bite-block can be made, for example, by introducing the bite-block filled with a material that can be shaped in a non-solidified form. The patient 91 then clenches his or her teeth about the bite-block and thereby the bite-block is shaped after the teeth and when the material of the bite-block has solidified, a cast of the teeth has been created. The bite-block 90 can be attached to the plates attached to the teeth by means of attachment elements 93, which for example, may be holes adapted to received corresponding balls of the attachment plates, or vice versa. Other embodiment may include, for example, means for attaching the bite-block by means of screws, snap connections, or stretched elastic bands.

Although specific constructions have been presented herein, it is to be understood that these are for illustrative purposes only. Various modifications and adaptations will be apparent to those skilled within the art. In view of possible modifications, it will be appreciated that the scope of the present invention should be determined by reference to the claims appended hereto.

The invention claimed is:

1. A patient fixation device for fixating a head of a patient with respect to a treatment unit as a preparation for or during treatment of the head, said patient fixation device being adapted to be attached to a stereotactic frame structure connected to said treatment unit, comprising:
   attachment fittings adapted to be releasably attached to corresponding attachment plates that are attached to teeth of the maxilla of said patient, each attachment plate being fixated to at least one tooth by a glue, wherein said attachment fittings are configured to be removable from said attachment plates that are attached to said patient and reattachable to the corresponding attachment plates in an identical orientation with respect to said frame structure and said teeth of said patient.

2. The patient fixation device according to claim 1, wherein said patient fixation device being adapted to be releasably attached to the stereotactic frame structure connected to said treatment unit.

3. The patient fixation device according to claim 2, including an interface unit adapted to be releasably mounted in said frame structure and wherein said attachment fittings is connected to said interface unit.

4. The patient fixation device according to claim 2, wherein said attachment fittings comprises:
   a first attachment member including a first attachment element adapted to be releasably attached to a corresponding at least one first attachment plate;
   a second attachment member including a second attachment element adapted to be releasably attached to a corresponding at least one second attachment plate; and
   a third attachment member including a third attachment element adapted to be releasably attached to a corresponding at least one third attachment plate.

5. The patient fixation device according to claim 1, including an interface unit adapted to be releasably mounted in said frame structure and wherein said attachment fittings is connected to said interface unit.

6. The patient fixation device according to claim 5, wherein said attachment fittings comprises:
   a first attachment member including a first attachment element adapted to be releasably attached to a corresponding at least one first attachment plate;
   a second attachment member including a second attachment element adapted to be releasably attached to a corresponding at least one second attachment plate; and
   a third attachment member including a third attachment element adapted to be releasably attached to a corresponding at least one third attachment plate.

7. The patient fixation device according to claim 1, wherein said attachment fittings comprises:
   a first attachment member including a first attachment element adapted to be releasably attached to a corresponding at least one first attachment plate;
   a second attachment member including a second attachment element adapted to be releasably attached to a corresponding at least one second attachment plate; and
   a third attachment member including a third attachment element adapted to be releasably attached to a corresponding at least one third attachment plate.

8. The patient fixation device according to claim 7, wherein said first attachment member includes a first arm being pivotally connected to said interface unit to allow said first arm to be adjusted with respect to said interface unit in two dimensions, said first arm including said first attachment element arranged at a distal part of said first arm; and wherein said second attachment member includes a second arm being pivotally connected to said interface unit to allow said second arm to be adjusted with respect to said interface unit in two dimensions, said second arm including said second attachment element arranged at a distal part of said second arm.

9. The patient fixation device according to claim 8, wherein said first arm and second arm are connected to each other by a locking element and wherein each of said first arm and said second arm is connected to said interface unit via pivot means, wherein said first arm and said second arm can be turned with respect to said interface unit and with respect to each other in two dimensions in an un-locked state and can be fixated with respect to said interface unit and with respect to each other in a locked state.

10. The patient fixation device claim 7, wherein said third attachment member includes a third arm and said third attachment element arranged at a distal end of said third arm and being adapted for releasable connection to a corresponding attachment plate, wherein said third arm is pivotally connected to said interface unit.

11. The patient fixation device according to claim 10, wherein said third arm of said third attachment member is connected to said interface unit by a ball and socket joint, wherein said third arm can be adjusted in three dimensions with respect to said interface unit in an un-locked state.

12. The patient fixation device according to claim 1, wherein said attachment fittings adapted to be releasably attached to corresponding attachment plates attached to teeth of the maxilla of said patient is a bite-block shaped as a cast of the teeth of the maxilla of the patient.

13. The patient fixation device according to claim 1, wherein said attachment fittings comprises fiducials, said fiducials being radio-opaque markers for computer tomography (CT) scanning or magnetic resonance markers for magnetic resonance (MR) scanning.

14. A method for fixating a head of a patient with respect to a treatment unit as a preparation for or during treatment of the head using a fixation system according to claim 13, said method comprising, not necessarily in order:
   fixating the attachment plates on teeth of the maxilla of the patient, each attachment plate being fixated to at least one tooth by a glue;
   positioning a patient for a first medical procedure;
   attaching said interface unit to the stereotactic frame structure;
   attaching said attachment fittings to corresponding attachment plates provided on teeth of the maxilla of said patient;
   performing the first medical procedure on the patient;
   removing said attachment fittings after completion of said first medical procedure; and
   re-attaching said attachment fittings to corresponding attachment plates provided on teeth of the maxilla of said patient a later time, wherein the attachment fittings is re-attached to the corresponding attachment plates that are attached to said patient in an identical orientation with respect to said frame structure and said teeth of said patient as when the attachment fittings was previously attached.

15. A patient fixation system for fixating a head of a patient with respect to a treatment unit during treatment of the head, said patient fixation system being adapted to be attached to a stereotactic frame structure connected to said treatment unit, comprising:

attachment plates adapted to be attached on teeth of the maxilla of said patient, each attachment plate being fixated to at least one tooth by a glue; and attachment fittings adapted to be releasably attached to corresponding attachment plates wherein said attachment fittings are configured to be movable from said attachment plates that are attached to said patient and reattachable to the corresponding attachment plates in an identical orientation with respect to said frame structure and said teeth of said patient.

16. The system according to claim 15, wherein said attachment fittings adapted to be releasably attached to corresponding attachment plates attached to teeth of the maxilla of said patient is a bite-block shaped as a cast of the teeth of the maxilla of the patient.

17. The system according to claim 15, wherein said patient fixation system being adapted to be releasable attached to the stereotactic frame structure connected to said treatment unit.

18. The system according to claim 15, further comprising an interface unit adapted to be releasably mounted in said frame structure and wherein said attachment fittings is connected to said interface unit.

19. The system according to claim 15, wherein said attachment fittings comprises:

a first attachment member including a first attachment element adapted to be releasably attached to a corresponding at least one first attachment plate;

a second attachment member including a second attachment element adapted to be releasably attached to a corresponding at least one second attachment plate; and a third attachment member including a third attachment element adapted to be releasably attached to a corresponding at least one third attachment plate.

20. The system according to claim 15, wherein said attachment fittings comprises fiducials, said fiducials being radio-opaque markers for computer tomography (CT) scanning or magnetic resonance markers for magnetic resonance (MR) scanning.

* * * * *